(12) United States Patent
Starobin et al.

(10) Patent No.: US 10,076,259 B2
(45) Date of Patent: Sep. 18, 2018

(54) METHOD AND SYSTEM FOR EVALUATING STABILITY OF CARDIAC PROPAGATION RESERVE

(71) Applicants: University of North Carolina Greensboro, Greensboro, NC (US); Duke University, Durham, NC (US)

(72) Inventors: Joseph M. Starobin, Greensboro, NC (US); Vivek Varadarajan, Greensboro, NC (US); Wanda Krassowska Neu, Durham, NC (US); Salim F. Idriss, Durham, NC (US)

(73) Assignees: University of North Carolina Greensboro, Greensboro, NC (US); Duke University, Durham, NC (US)

( * ) Notice: Subject to any disclaimer, the term of this patent is extended or adjusted under 35 U.S.C. 154(b) by 0 days.

(21) Appl. No.: 15/134,881

(22) Filed: Apr. 21, 2016

(65) Prior Publication Data

US 2016/0287123 A1    Oct. 6, 2016

Related U.S. Application Data

(63) Continuation of application No. 14/130,363, filed as application No. PCT/US2012/044672 on Jun. 28, 2012, now abandoned.

(60) Provisional application No. 61/506,289, filed on Jul. 11, 2011.

(51) Int. Cl.
*A61N 1/362* (2006.01)
*A61B 5/0452* (2006.01)
*A61B 5/00* (2006.01)
*A61B 5/04* (2006.01)
*A61B 5/024* (2006.01)
*A61B 5/0464* (2006.01)

(52) U.S. Cl.
CPC ............ *A61B 5/0452* (2013.01); *A61B 5/024* (2013.01); *A61B 5/04012* (2013.01); *A61B 5/04017* (2013.01); *A61B 5/486* (2013.01); *A61B 5/4884* (2013.01); *A61N 1/362* (2013.01); *A61B 5/0464* (2013.01)

(58) Field of Classification Search
CPC ... A61B 5/0402; A61B 5/0452; A61B 5/0464; A61B 5/7246; A61B 5/7264; A61B 5/7275; A61B 5/7282
USPC .................................................. 607/508, 509
See application file for complete search history.

(56) References Cited

U.S. PATENT DOCUMENTS 5,419,338 A    5/1995  Sarma et al.
5,437,285 A    8/1995  Verrier et al.
5,560,368 A   10/1996  Berger
(Continued)

OTHER PUBLICATIONS

International Search Report and Written Opinion, PCT/US2012/044672, dated Jan. 3, 2013.
(Continued)

*Primary Examiner* — Allen Porter, Jr.
(74) *Attorney, Agent, or Firm* — Myers Bigel, P.A.

(57) ABSTRACT

A method of determining the susceptibility to ventricular arrhythmias in a subject, the method including determining a reserve of refractoriness (RoR) and a reserve of memory (RoM) and combining the reserve of refractoriness (RoR) and the reserve of memory (RoM) to produce a metric of stability-of-propagation reserve (SoPR) in the subject, a higher value of SoPR indicating lower susceptibility to ventricular arrhythmias in the subject. Systems and apparatus for carrying out the method are also described.

17 Claims, 6 Drawing Sheets

(56) References Cited

U.S. PATENT DOCUMENTS

| | | |
|---|---|---|
| 5,713,367 A | 2/1998 | Arnold et al. |
| 5,951,484 A | 9/1999 | Hoium et al. |
| 6,361,503 B1 | 3/2002 | Starobin et al. |
| 7,123,953 B2 | 10/2006 | Starobin et al. |
| 7,313,437 B2 | 12/2007 | Jordan et al. |
| 8,346,351 B2 | 1/2013 | Hadley |

OTHER PUBLICATIONS

Attwell et al. "The effects of heart rate on the action potential of guinea-pig and human ventricular muscle" J. Physiol., 313: 439-461, 1981.

Chernyak et al. "Class of exactly solvable models of excitable media" Phys. Rev. Lett., 80: 5675-5678, 1998a.

Chernyak et al. "Where do dispersion curves end? A basic question in theory of excitable media" Phys. Rev. E, 58: R4108-R4111, 1998b.

Daubert et al. "Predictive value of ventricular arrhythmia inducibility for subsequent ventricular tachycardia or ventricular fibrillation in Multicenter Automatic Defibrillator Implantation Trial (MADIT) II patients", J. Am. Coll. Cardiol.. 47: 98-107 2006.

Davidenko et al. "Rate dependence and supernormality in excitability of guinea pig papilary muscle" Am. J. Physiol.—Heart and Circul. Physiol., 259: H290-H299, 1990.

Fenton et al. "Multiple mechanisms of spiral wave breakup in a model of cardiac electrical activity", Chaos, 12: 852-892, 2002.

Franz et al. "The electrical restitution curve revisited: steep or flat slope—Which is better?", J. Cardiovasc. Electrophysiol., 14: S140-S147, 2003.

Haghjoo et al. "Microvolt T-wave alternans: A review of techniques, interpretation, utility, clinical studies, and future perspectives", Int. J. Cardiol., 109: 293-306, 2006.

Ideker et al. "Steepness of the restitution curve: A slippery slope?" J. Cardiovasc. Electrophysiol., 13: 1173-1175, 2002.

Kalb et al. "The restitution portrait: A new method for investigating rate-dependent restitution", J. Cardiovasc. Electrophysiol., 15: 698-709, 2004.

Kusmirek et al. "Sudden cardiac death: The role of risk stratification", Am. Heart J., 153: S25-S33, 2007.

Lloyd-Jones et al. "Heart disease and stroke statistics 2009 update. A report from the American Heart Association Statistics Committee and Stroke Statistics Subcommittee", Circulation, 119: pp. e1-e161, 2009.

Myles et al. "The link between repolarisation alternans and ventricular arrhythmia: Does the cellular phenomenon extend to the clinical problem?", J. Mol. Cell. Cardiol., 45: 1-10, 2008.

Pitruzzello et al. "Spatial heterogeneity of the restitution portrait in rabbit epicardium", Am. J. Physiol., 292: H1568-H1578, 2007.

Polotski et al. "Relation between cardiac restitution and flow limitation in an experimental model of coronary artery disease", J. Electrocardiol., 41: 646, 2008.

Press et al. Numerical Recipies in Fortran 77, Cambridge Press, 1992.

Ravens et al. "Electrophysiological aspects of changes in heart rate", Basic Res. Cardiol., 93, Suppl. 1: 60-65, 1998.

Schaeffer et al. "An ionically based mapping model with memory for cardiac restitution", Bull. Math. Biol., 69: 459-482, 2007.

Starobin et al. "Wavelet formation in excitable cardiac tissue: The role of wavefront-obstacle interactions in initiating high-frequency fibrillatory-like arrhythmias", Biophys. J., 70: 581-594, 1996.

Starobin et al. "Identifying coronary artery flow reduction and ischemia using quasistationary QT/RR-interval hysteresis measurements", J. Electrocard., 40: S91-S96, 2007.

Starobin et al. "Critical scale of propagation influences dynamics of waves in a model of excitable medium", Nonlinear Biomedical Physics, vol. 3, art. 4, 2009.

Varadarajan et al. "Assessing QT-RR interval hysteresis in 12-lead electrograms", In Proceedings: Computers in Cardiology, 36:273-276, 2009.

Qu Z et al. Vulnerable window for conduction block in a one-dimensional cable of cardiac cells, 1: single extrasystoles. Biophysical Journal. Aug. 2006; 91: 793-804.

Rabinovitch, A, et al., "Inwards Propogating Waves with a Limit Cycle Medium," Physical Review Letters, vol. 87, No. 8, Aug. 20, 2001, 4 pages.

Starobin, JM, et al., "Evaluation of Restitution Slopes Using a Quasi-stationary Exercise Protocol," Computing in Cardiology 2010; 37: 777-780.

A

B

METHOD AND SYSTEM FOR EVALUATING STABILITY OF CARDIAC PROPAGATION RESERVE

RELATED APPLICATIONS

This application is continuation application of and claims priority to U.S. patent application Ser. No. 14/130,363, filed Apr. 28, 2014, now abandoned, which is a 35 U.S.C. § 371 national phase entry of PCT Application PCT/US2012/044672, filed Jun. 28, 2012, and published in English on Jan. 17, 2013, as International Publication No. WO 2013/009486, and which claims the benefit under 35 U.S.C. § 119(e) of U.S. Provisional Patent Application No. 61/506,289, filed Jul. 11, 2011, the disclosure of each of which is incorporated herein by reference in its entirety.

FIELD OF THE INVENTION

The present invention concerns methods, systems and apparatus for detecting risk of ventricular arrhythmias in a subject.

BACKGROUND OF THE INVENTION

Each year approximately 310,000 Americans die of sudden cardiac death (SCD) from ventricular tachyarrhythmias [Lloyd-Jones 2009]. The first preventive step toward reducing mortality from SCD is to identify individuals at risk for developing arrhythmias. Yet, despite years of research, the risk stratification strategies are unclear and there are still no reliable clinical tests that predict who is susceptible to this potentially lethal heart rhythm disorders [Kusmirek & Gold 2007].

Currently, the most reliable method of assessing vulnerability to cardiac arrhythmias is EP testing, in which a provocative intracardiac pacing protocol is applied to the patient with an aim of inducing an arrhythmia episode [Daubert 2006]. EP testing is an invasive procedure and carries a non-negligible risk of death. In contrast, the present invention can evaluate stability-of-propagation reserve (SoPR) from data collected either invasively or noninvasively. Even if invasive data collection is used, the pacing protocol for determination of the SoPR is significantly less aggressive and provocative than standard intracardiac arrhythmia inducibility protocols. Thus, the risk to the patient is well below the risk of current EP testing.

Of the noninvasive methods, the most successful is the T-wave alternans (TWA) testing [Hayhjoo 2006], which detects a low-amplitude beat-to-beat fluctuation of the ECG T-wave. TWA reflects cellular alternans, i.e., long-short alternation in action potential duration (APD). Theory of excitable media and nonlinear dynamics predict that APD alternans can result in a unidirectional conduction block, reentry, and the onset of a tachyarrhythmia [Myles 2008]. However, alternans is only one possible route to a fatal arrhythmia (FIG. 1). Conduction blocks can occur without prior alternans. For example, unidirectional conduction block may occur in response to a premature stimulus applied to the tissue with a critical level of refractoriness, or wavebreak and conduction block may occur when there is interaction with a less excitable portion of cardiac tissue [Starobin 1996, Fenton 2002].

Because TWA predicts just one of possible precursors of arrhythmia, it works well only in a limited group of the highest-risk patients with a history of sustained ventricular arrhythmias [Kismirek & Gold 2007]. In contrast, the present invention predicts the likelihood of conduction block, not just one of its precursors. Therefore, it should capture a wider range of proarrhythmic states and work in a broader population of patients at risk. In addition, the present invention can be implemented using current commercial ECG exercise testing equipment, while TWA testing requires special instrumentation to detect microvolt-level alternans.

SUMMARY OF THE INVENTION

Among other things, the present invention identifies patients who are susceptible to instabilities in propagation of cardiac electrical excitation waves, which are among the most prevalent and dangerous causes of SCD.

A first aspect of the invention is a method of determining the susceptibility to ventricular arrhythmias in a subject, comprising the steps of:

(a) collecting (e.g., by surface EKG or intracardiac EKG) at least one QT and diastolic interval (DI) interval data set (e.g., from 100 to 1,000 QT and DI intervals) from the subject during a stage of gradually increasing heart rate or a stage of gradually decreasing heart rate;

(b) determining (e.g., by applying low- and high pass filtering) low-frequency QT-DI interval trends and high-frequency QT-DI fluctuation signals in said at least one QT and DI interval data set;

(c) finding a plurality of (or in some embodiments all) correlated and anti-correlated portions between said high-frequency QT-DI fluctuation signals;

(d) determining (e.g., by linear regression analysis) corresponding regression lines for said correlated and anti-correlated portions;

(e) finding a plurality of (or in some embodiments all) steady state QT-DI points designated by intersections between said low frequency QT-DI trends and said corresponding regression lines;

(f) fitting action potential durations computed from a rate dependent reaction-diffusion model to corresponding ones of said steady state QT-DI points to give (i) a model excitation threshold and (ii) a minimal level of refractoriness at a plurality of (or in some embodiments all of) said steady state QT-DI points;

(g) at the steady state QT-DI point corresponding to the highest heart rate in said QT and DI interval data set, determining the difference between said minimal level of refractoriness and a model critical excitation threshold for a stable solitary pulse corresponding to the rate dependent reaction diffusion model of step (f) to give a reserve of refractoriness (RoR);

(h) fitting action potential durations computed from a rate dependent reaction-diffusion model to said correlated and anti-correlated portions to give a rate of adaptation of each model excitation threshold to a corresponding steady state value at a plurality of (or in some embodiments all of) said steady state QT-DI points;

(i) at the steady state QT-DI point corresponding to the highest heart rate in said QT and DI interval data set, determining the inverse of said rate of adaptation to give a reserve of memory (RoM);

(j) combining said reserve of refractoriness (RoR) and said reserve of memory (RoM) to produce a metric of stability-of-propagation reserve (SoPR) in said subject, a higher value of SoPR indicating (e.g., a higher level of stability of propagating excitation wave and) lower susceptibility to ventricular arrhythmias in said subject.

A further aspect of the invention is a method of determining susceptibility to ventricular arrhythmias in a subject, comprising the steps, performed on a computer system, of:

(a) providing at least one QT and DI interval data set (e.g., from 100 to 1,000 QT and DI intervals) collected from the subject during a stage of gradually increasing heart rate or a stage of gradually decreasing heart rate;

(b) determining low-frequency QT-DI interval trends and high-frequency QT-DI fluctuation signals in said at least one QT and DI interval data set;

(c) finding a plurality of (or in some embodiments all) correlated and anti-correlated portions between said high-frequency QT-DI fluctuation signals;

(d) determining corresponding regression lines for said correlated and anti-correlated portions;

(e) finding a plurality of (or in some embodiments all) steady state QT-DI points designated by intersections between said low frequency QT-DI trends and said corresponding regression lines;

(f) fitting action potential durations computed from a rate dependent reaction-diffusion model to corresponding ones of said steady state QT-DI points to give (i) a model excitation threshold and (ii) a minimal level of refractoriness at a plurality of (or in some embodiments all of) said steady state QT-DI points;

(g) at the steady state QT-DI point corresponding to the highest heart rate in said QT and DI interval data set, determining the difference between said minimal level of refractoriness and a model critical excitation threshold for a stable solitary pulse corresponding to the rate dependent reaction diffusion model of step (f) to give a reserve of refractoriness (RoR);

(h) fitting action potential durations computed from a rate dependent reaction-diffusion model to said correlated and anti-correlated portions to give a rate of adaptation of each model excitation threshold to a corresponding steady state value at a plurality of (or in some embodiments all of) said steady state QT-DI points;

(i) at the steady state QT-DI point corresponding to the highest heart rate in said QT and DI interval data set, determining the inverse of said rate of adaptation to give a reserve of memory (RoM);

(j) combining said reserve of refractoriness (RoR) and said reserve of memory (RoM) to produce a metric of stability-of-propagation reserve (SoPR) in said subject, a higher value of SoPR indicating (e.g., a higher level of stability of propagating excitation wave and) lower susceptibility to ventricular arrhythmias in said subject.

A further aspect of the invention is a computer system for determining susceptibility to ventricular arrhythmias in a subject, said system comprising:

(a) means for providing at least one QT and DI interval data set (e.g., from 100 to 1,000 QT and DI intervals) collected from the subject during a stage of gradually increasing heart rate or a stage of gradually decreasing heart rate;

(b) means for determining low-frequency QT-DI interval trends and high-frequency QT-DI fluctuation signals in said at least one QT and DI interval data set;

(c) means for finding a plurality of (or in some embodiments all) correlated and anti-correlated portions between said high-frequency QT-DI fluctuation signals;

(d) means for determining corresponding regression lines for said correlated and anti-correlated portions;

(e) means for finding a plurality of (or in some embodiments all) steady state QT-DI points designated by intersections between said low frequency QT-DI trends and said corresponding regression lines;

(f) means for fitting action potential durations computed from a rate dependent reaction-diffusion model to corresponding ones of said steady state QT-DI points to give (i) a model excitation threshold and (ii) a minimal level of refractoriness at a plurality of (or in some embodiments all of) said steady state QT-DI points;

(g) means for, at the steady state QT-DI point corresponding to the highest heart rate in said QT and DI interval data set, determining the difference between said minimal level of refractoriness and a model critical excitation threshold for a stable solitary pulse corresponding to the rate dependent reaction diffusion model of step (f) to give a reserve of refractoriness (RoR);

(h) means for fitting action potential durations computed from a rate dependent reaction-diffusion model to said correlated and anti-correlated portions to give a rate of adaptation of each model excitation threshold to a corresponding steady state value at a plurality of (or in some embodiments all of) said steady state QT-DI points;

(i) means for, at the steady state QT-DI point corresponding to the highest heart rate in said QT and DI interval data set, determining the inverse of said rate of adaptation to give a reserve of memory (RoM);

(j) means for combining said reserve of refractoriness (RoR) and said reserve of memory (RoM) to produce a metric of stability-of-propagation reserve (SoPR) in said subject, a higher value of SoPR indicating (e.g., a higher level of stability of propagating excitation wave and) lower susceptibility to ventricular arrhythmias in said subject.

A still further aspect of the invention is a computer program product for determining susceptibility to ventricular arrhythmias in a subject from (a) at least one QT and DI interval data set (e.g., from 100 to 1,000 QT and DI intervals) collected from the subject during a stage of gradually increasing heart rate or a stage of gradually decreasing heart rate, said computer program product comprising a computer usable storage medium having computer readable program code means embodied in the medium, the computer readable program code means comprising:

(b) computer readable program code means for determining low-frequency QT-DI interval trends and high-frequency QT-DI fluctuation signals in said at least one QT and DI interval data set;

(c) computer readable program code means for finding a plurality of (or in some embodiments all) correlated and anti-correlated portions between said high-frequency QT-DI fluctuation signals;

(d) computer readable program code means for determining corresponding regression lines for said correlated and anti-correlated portions;

(e) computer readable program code means for finding a plurality of (or in some embodiments all) steady state QT-DI points designated by intersections between said low frequency QT-DI trends and said corresponding regression lines;

(f) computer readable program code computer readable program code means for fitting action potential durations computed from a rate dependent reaction-diffusion model to corresponding ones of said steady state QT-DI points to give (i) a model excitation threshold and (ii) a minimal level of refractoriness at a plurality of (or in some embodiments all of) said steady state QT-DI points;

(g) computer readable program code means for, at the steady state QT-DI point corresponding to the highest heart rate in said QT and DI interval data set, determining the difference between said minimal level of refractoriness and a model critical excitation threshold for a stable solitary pulse corresponding to the rate dependent reaction diffusion model of step (f) to give a reserve of refractoriness (RoR);

(h) computer readable program code means for fitting action potential durations computed from a rate dependent reaction-diffusion model to said correlated and anti-correlated portions to give a rate of adaptation of each model excitation threshold to a corresponding steady state value at a plurality of (or in some embodiments all of) said steady state QT-DI points;

(i) computer readable program code means for, at the steady state QT-DI point corresponding to the highest heart rate in said QT and DI interval data set, determining the inverse of said rate of adaptation to give a reserve of memory (RoM);

(j) computer readable program code means for combining said reserve of refractoriness (RoR) and said reserve of memory (RoM) to produce a metric of stability-of-propagation reserve (SoPR) in said subject, a higher value of SoPR indicating (e.g., a higher level of stability of propagating excitation wave and) lower susceptibility to ventricular arrhythmias in said subject.

The present invention makes use, in part, of aspects of the analysis of QT and RR interval variability described in Starobin and Chernyak, U.S. Pat. No. 7,123,953 (the disclosure of which is incorporated by reference herein in its entirety). However, there is a fundamental difference in the way this analysis is used for prediction of cardiac instabilities. The Starobin-Chernyak method is based on the analysis of correlation of QT and RR interval fluctuations collected during gradual changes of exercise load. The correlation coefficient normalized by the slope of a steady state restitution curve computed at the maximum heart rate is used as the aggregate index of stability. The present invention goes beyond the measurement-derived index: the SoPR is evaluated from a reaction-diffusion model, whose parameters are customized for an individual patient.

An advantage of the present invention over the Starobin-Chernyak method is that their aggregate index depends on the slope of the steady state restitution curve, which is not reliable indicator of stability of propagation [Ideker 2002]. For example, the magnitude of this index can vary due to flattening of restitution curves during myocardial ischemia [Franz 2003], which prevents the accurate assessment of instabilities. Indeed, the index decreases at higher heart rates when propagation of the excitation wave is more prone to instabilities caused by enhanced interactions with spatial inhomogeneities during ischemia. Our initial model-based investigation of SoPR shows that the present invention will be free from this limitation.

Other major non-invasive methods of assessing an individual's susceptibility to cardiac arrhythmias include different types of assessment of the QT and/or RR interval variability, both spatial and temporal (U.S. patents by Chamoun U.S. Pat. No. 5,020,540, 1991; Wang U.S. Pat. No. 4,870,974, 1989; Kroll et al. U.S. Pat. No. 5,117,834, 1992; Henkin et al. U.S. Pat. No. 5,323,783, 1994; Xue et al. U.S. Pat. No. 5,792,065, 1998; Lander U.S. Pat. No. 5,827,195, 1998; Lander et al. U.S. Pat. No. 5,891,047, 1999; Hojum et al. U.S. Pat. No. 5,951,484, 1999). These methods are different from the present invention because they are linked to specific types of spatial and temporal inhomogeneities. Thus, in contrast to SoPR, they cannot predict instabilities that are developing in structurally homogeneous cardiac muscle.

The present invention is explained in greater detail in the drawings herein and the specification set forth below.

DETAILED DESCRIPTION OF EMBODIMENTS OF THE INVENTION

Figure 1:
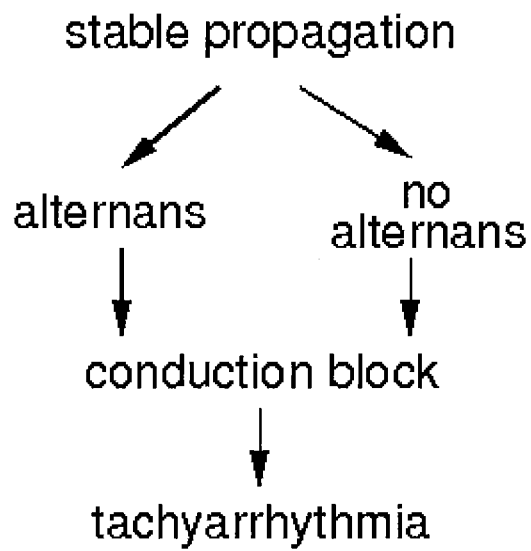
FIG. 1. Possible routes to arrhythmia.

The present invention is explained in greater detail below. This description is not intended to be a detailed catalog of all the different manners in which particular elements of the invention can be implemented, and numerous variations will be apparent to those skilled in the art based upon the instant disclosure.

As will be appreciated by one of skill in the art, certain aspects of the present invention may be embodied as a method, data processing system, or computer program product. Accordingly, certain aspects of the present invention may take the form of an entirely hardware embodiment, an entirely software embodiment, or an embodiment combining software and hardware aspects. Furthermore, certain aspects of the present invention may take the form of a computer program product on a computer-usable storage medium having computer readable program code means embodied in the medium. Any suitable computer readable medium may be utilized including, but not limited to, hard disks, CD-ROMs, optical storage devices, and magnetic storage devices.

Certain aspects of the present invention are described below with reference to flowchart illustrations of methods, apparatus (systems), and computer program products. It will be understood that each block of the flowchart illustrations, and combinations of blocks in the flowchart illustrations, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

Computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

Computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Definitions

"Ventricular arrhythmia" as used herein refers to any type of ventricular arrhythmias. Examples include, but are not limited to, premature ventricular and supraventricular contractions, ventricular and supraventricular tachycardias and ventricular and supraventricular fibrillation.

"Exercise" as used herein refers to voluntary skeletal muscle activity of a subject that increases heart rate above that found at a sustained stationary resting state. Examples of exercise include, but are not limited to, cycling, rowing, weight-lifting, walking, running, stair-stepping, etc., which may be implemented on a stationary device such as a treadmill or in a non-stationary environment.

"Exercise load" or "load level" refers to the relative strenuousness of a particular exercise, with greater loads or load levels for a given exercise producing a greater heart rate in a subject. For example, load may be increased in weight-lifting by increasing the amount of weight; load may be increased in walking or running by increasing the speed and/or increasing the slope or incline of the walking or running surface; etc.

"Gradually increasing" and "gradually decreasing" an exercise load refers to exercise in which the subject is caused to perform an exercise under a plurality of different sequentially increasing or sequentially decreasing loads. The number of steps in the sequence can be infinite so the terms gradually increasing and gradually decreasing loads include continuous load increase and decrease, respectively.

"Electrocardiogram" or "ECG" refers to a continuous or sequential record (or a set of such records) of a local electrical potential field obtained from one or more locations outside the cardiac muscle. This field is generated by the combined electrical activity (action potential generation) of multiple cardiac cells. The recording electrodes may be either subcutaneously implanted or may be temporarily attached to the surface of the skin of the subject, usually in the thoracic region. An ECG record typically includes the single-lead ECG signal that represents a potential difference between any two of the recording sites including the site with a zero or ground potential.

"Quasi-stationary conditions" refer to any situation in which a gradual change in the external, conditions and/or the physiological response it causes occurs slower than any corresponding adjustment due to sympathetic/parasympathetic and hormonal control. If the representative time of the external conditions variation is denoted by $\tau_{ext}$, and $\tau_{int}$ is a representative time of the fastest of the internal, sympathetic/parasympathetic and hormonal control, then "quasi-stationary conditions" indicates $\Sigma_{ext} \gg \tau_{int}$ (e.g., $\tau_{ext}$ is at least about two, three, four or five times greater than $\tau_{int}$). Abrupt changes in exercise load may be either quasi-stationary or non-quasi-stationary. "A non-quasi-stationary abrupt change" refers to a situation opposite quasi-stationary conditions corresponding to a sufficiently fast change in the external conditions as compared with the rate sympathetic/parasympathetic and hormonal control—that is, it requires that $\tau_{ext} \ll \tau_{int}$ (e.g., $\tau_{ext}$ is at least about two, three, for our five times less than $\tau_{int}$). "A quasi-stationary abrupt change" refers to a relatively fast change in exercise load that is nonetheless quasi-stationary-, for example, because the change is preceded by a sufficiently high exercise load such that a slower, quasi-stationary recovery period is observed.

"QT and DI data set" refers to a record of the time course of an electrical signal comprising action potentials spreading through cardiac muscle. Any single lead ECG record incorporates a group of three consecutive sharp deflections usually called a QRS complex and generated by the propagation of the action potential's front through the ventricles. In contrast, the electrical recovery of ventricular tissue is seen on the ECG as a relatively small deflection known as the T wave. The time interval between the cardiac cycles (i.e., between the maxima of the consecutive R waves) is called a RR interval, while the action potential duration (i.e., the time between the beginning of a QRS complex and the end of the ensuing T wave) is called a QT interval. Alternative definitions of these intervals can be equivalently used in the framework of the present invention. For example, an RR interval can be defined as the time between any two similar points, such as the similar inflection points, on two consecutive R waves, or in any other manner to measure cardiac cycle length. A QT interval can be defined as the time interval between the peak of the Q wave and the peak of the T wave. It can also be defined as the time interval between the beginning (or the center) of the Q wave and the end of the ensuing T wave defined as the point on the time axis (the base line) at which it intersects with the linear extrapolation of the T wave's falling branch and started from its inflection point, or in any other manner to measure action potential duration. A diastolic interval (DI) is the difference between RR and QT intervals, so DI=RR−QT. An ordered set of such interval durations simultaneously with the time instants of their beginnings or ends which are accumulated on a beat to beat basis or on any given beat sampling rate basis form a corresponding QT and DI interval data set.

A "trend" on a data segment is a data set generally obtained from the raw data segment by low-pass filtering under the restriction that the deviations from the resulting trend have zero sum. In a particular implementation herein, a trend is assessed as the smoothest data set obtained by fitting the raw data on the segment with a lowest degree polynomial (linear or quadratic, the latter being used when the data set encompasses a single extremum, i.e. a minimum or a maximum). The total variation of the trend is always much smaller than the total variation of the raw data segment.

A "stationary data segment" is a data segment with a negligible variation in its trend.

A "slow trend" is a trend with a small but not negligible variation. A trend obtained under the quasi-stationary protocol is a slow trend. A duration of a stage during which the data incorporating a slow trend are collected must be approximately an order of magnitude (e.g., at least about two, three, four, five or ten times) longer than the average duration (~1 minute) of the heart rate adjustment after an abrupt stop of exercise from a peak load rate (typically from 120 to 150 beat/min) to the rest rate (typically from 50 to 70 beat/min).

A "fluctuation" or "fast fluctuation" of a QT or RR interval on a data segment as used herein refers to a set of zero sum deviations from a QT (or, respectively, RR) slow trend corresponding to this particular data segment. A traditional measure of fluctuations is the standard root-mean-square deviation (STD). A typical value of STD for QT (or RR) interval fluctuations is of an order of magnitude (e.g., at least about two, three, four, five or ten times) smaller than the total variation of the QT (or, respectively, RR) interval trend during the entire load stage under quasi-stationary conditions.

"Instantaneous restitution dependences" refer to curves representing QT-interval fluctuations versus RR-interval fluctuations, fluctuations being understood as the zero sum deviations from the corresponding QT and RR slow trends.

Methods.

The methods of the present invention are primarily intended for the testing of human subjects. Virtually any human subject can be tested by the methods of the present invention, including male, female, juvenile, infant, adolescent, adult, and geriatric subjects. The methods may be carried out as an initial screening test on subjects for whom no substantial previous history or record is available, or may be carried out on a repeated basis on the same subject (particularly where a comparative quantitative indicium of an individual's cardiac health over time is desired) to assess the effect or influence of intervening events and/or intervening therapy on that subject between testing sessions.

As noted above, the method of the present invention generally comprises (a) collecting at least one QT and DI interval data set from the subject during (i) a stage of gradually increasing heart rate, (ii) a stage of gradually decreasing heart rate, or (iii) both a stage of gradually increasing heart rate and gradually decreasing heart rate.

The stages of gradually increasing and/or gradually decreasing heart rate are carried out during a gradual exercise protocol in a manner that maintains during these periods essentially or substantially the same stimulation of the heart by the peripheral nervous and hormonal control systems. These stages can be also found and selected from arbitrary continuous Holter monitoring records. This methodology can be carried out by a variety of techniques, with the technique of conducting or selecting one and/or several consecutive or isolated stages of gradually increasing and gradually decreasing average heart rates.

The stage of gradually increased average heart rate and the stage of gradually decreased average heart rate may be the same in duration or may be different in duration. In general, each stage is at least 3, 5, 8, or 10 minutes or more in duration. Together, the duration of the two stages may be from about 6, 10, 16 or 20 minutes in duration to about 30, 40, or 60 minutes in duration or more. The two stages are preferably carried out sequentially in time—that is, with one stage following after the other substantially immediately, without an intervening rest stage. In the alternative, the two stages may be carried out separately in time, with an intervening "plateau" stage (e.g., of from 1 to 5 minutes) during which cardiac stimulation or exercise load is held substantially constant, before the stage of decreasing load is initiated. One and/or several gradual slow trend stages can be selected from the continuous Holter recording in the same manner.

The exercise protocol may include the same or different sets of load steps during the stages of increasing or decreasing heart rates. For example, the peak load in each stage may be the same or different, and the minimum load in each stage may be the same or different. In general, each stage consists of at least two or three different load levels, in ascending or descending order depending upon the stage. Relatively high load levels, which result in relatively high heart rates, can be used but are not essential. An advantage of the present invention is that its sensitivity allows both exercise procedures to be carried out at relatively low load levels that do not unduly increase the pulse rate of the subject. For example, the method may be carried out so that the heart rate of the subject during either the ascending or descending stage (or both) does not exceed about 140, 120, or even 100 beats per minute, depending upon the condition of the subject. Of course, data collected at heart rates above 100, 120, or 140 beats per minute may also be utilized if desired, again depending upon the condition of the subject.

For example, for an athletic or trained subject, for the first or ascending stage, a first load level may be selected to require a power output of 60 to 100 or 150 watts by the subject; an intermediate load level may be selected to require a power output of 100 to 150 or 200 watts by the subject; and a third load level may be selected to require a power output of 200 to 300 or 450 watts or more by the subject. For the second or descending stage, a first load level may be selected to require a power output of 200 to 300 or 450 watts or more by the subject; an intermediate or second load level may be selected to require a power output of 100 to 150 or 200 watts by the subject; and a third load level may be selected to require a power output of 60 to 100 or 150 watts by the subject. Additional load levels may be included before, after, or between all of the foregoing load levels as desired, and adjustment between load levels can be carried out in any suitable manner, including step-wise or continuously.

In a further example, for an average subject or a subject with a history of cardiovascular disease, for the first or ascending stage, a first load level may be selected to require a power output of 40 to 75 or 100 watts by the subject; an intermediate load level may be selected to require a power output of 75 to 100 or 150 watts by the subject; and a third load level may be selected to require a power output of 125 to 200 or 300 watts or more by the subject. For the second or descending stage, a first load level may be selected to require a power output of 125 to 200 or 300 watts or more by the subject; an intermediate or second load level may be selected to require a power output of 75 to 100 or 150 watts by the subject; and a third load level may be selected to require a power output of 40 to 75 or 100 watts by the subject. As before, additional load levels may be included before, after, or between all of the foregoing load levels as desired, and adjustment between load levels can be carried out in any suitable manner, including step-wise or continuously.

The heart rate may be gradually increased and gradually decreased by subjecting the patient to a predetermined schedule of stimulation. For example, the patient may be subjected to a gradually increasing exercise load and gradually decreasing exercise load, or gradually increasing electrical or pharmacological stimulation and gradually decreasing electrical or pharmacological stimulation, according to a predetermined program or schedule. Such a predetermined schedule is without feedback of actual heart rate from the patient. In the alternative, the heart rate of the patient may be gradually increased and gradually decreased in response to actual heart rate data collected from concurrent monitoring of said patient. Such a system is a feedback system. For example, the heart rate of the patient may be monitored during the test and the exercise load (speed and/or incline, in the case of a treadmill) can be adjusted so that the heart rate varies in a prescribed way during both stages of the test. The monitoring and control of the load can be accomplished by a computer or other control system using a simple control program and an output panel connected to the control system and to the exercise device that generates an analog signal to the exercise device. One advantage of such a feedback system is that (if desired) the control system can insure that the heart rate increases substantially linearly during all slow trend stages.

The present invention implements a method of evaluating the "stability-of-propagation reserve," a metric that measures the susceptibility to propagation instabilities and arrhythmia. SoPR combines two factors that determine the stability of propagation: refractoriness and memory. Sufficient level of medium refractoriness is necessary to support the propagation of an excitation wave. Our invention measures the reserve of refractoriness (RoR), defined as the difference between the minimum level of medium refractoriness and the critical threshold for a stable solitary pulse. Our invention also measures the short-term cardiac memory, which controls the rate of adaptation of medium excitation threshold from one steady state heart rate to another (RoM, rate of memory).

To determine SoPR for an individual patient, one needs to fit a reaction-diffusion model to the dynamics of the ECG intervals, QT and DI (diastolic interval, DI=RR−QT), measured in that patient. To obtain the most comprehensive characterization of the QT-DI dynamics, we use the concept of the "restitution portrait" (RP) developed in [Kalb 2004]. As a reaction-diffusion model, we use a modified two-variable Chernyak-Starobin-Cohen (CSC) with rate dependent excitation threshold [Starobin 2009]. This model has a limited number of parameters, which can be determined by fitting the RP computed by the model to the RP determined from QT and DI interval dynamics in an individual patient, which is not feasible with more complex models of cardiac membrane. Thus, the present invention allows patient-specific modeling and prediction of risk of propagation instabilities.

In some embodiments, the action potential durations are from 100 to 700 or 900 milliseconds in duration.

In some embodiments, the model excitation threshold (dimensionless) is from 0.05 or 0.1 to 0.6 or 1.

In some embodiments, the minimal level of refractoriness (dimensionless) is from 0.05 or 0.1 to 0.6 or 1.

In some embodiments, the highest heart rate in said QT and DI interval data set is 250 or 300 beats per minute.

In some embodiments, the model critical excitation threshold for a stable solitary pulse (dimensionless) is from 0.1 or 0.3 to 0.8 or 1.

In some embodiments, the reserve of refractoriness (dimensionless) is from zero to one.

In some embodiments, the rate of adaptation of each model excitation threshold (dimensionless) is 0.01 to 1.

In some embodiments, the reserve of memory (dimensionless) is from one to one hundred.

In some embodiments, the stability-of-propagation reserve (dimensionless) is from zero to one.

Testing Apparatus.

In an illustrative embodiment of the invention, electrocardiograms are recorded by an ECG recorder, via electrical leads placed on a subject's body. The ECG recorder may be, for example, a standard multi-lead Holter recorder or any other appropriate recorder. The analog/digital converter digitizes the signals recorded by the ECG recorder and transfers them to a personal computer, or other computer or central processing unit, through a standard external input/output port. The digitized ECG data can then be processed by standard computer-based waveform analyzer software. Restitution curves and a cardiac or cardiovascular health indicium or other quantitative measure of the presence, absence or degree of susceptibility to cardiac arrhythmias can then be calculated automatically in the computer through a program (e.g., Basic, Fortran, C++, etc.) implemented therein as software, hardware, or both hardware and software.

The present invention is explained in greater detail in the non-limiting examples set forth below.

Example 1

Reaction-Diffusion Model

Model Formulation.

We implement a modified Chernyak-Starobin-Cohen (CSC) reaction-diffusion model to fit experimental QT and DI intervals. The state variables of the CSC model are membrane potential u(x,t) and recovery variable v(x,t). Both u and v are dimensionless and take values between 0 and 1. The governing equations are:

$$\frac{\partial u}{\partial t} = \frac{\partial^2 u}{\partial x^2} - i(u, v) + P(x, t) \quad (1)$$

and $$\frac{\partial v}{\partial t} = \varepsilon(\zeta u + v_r - v),$$

where membrane current i(u,v) is given by:

$$i(u,v) = \lambda u \text{ for } u < v \text{ and } (u-1) \text{ for } u \geq v. \quad (2)$$

In (1-2), $\varepsilon$, $\zeta$, $\lambda$ and $v_r$ are model parameters and P(x,t) specifies the pacing pulses. At rest, u and v are equal to 0 and $v_r$, respectively. The potential u quickly increases to 1 during the upstroke, stays near 1 during the action potential (AP), and afterwards returns to zero. The recovery variable v moves slowly toward 1 during AP and starts decreasing after AP ends. For a solitary pulse, v eventually returns to $v_r$.

Parameter $v_r$ and the Critical Excitation Threshold.

Figure 2:
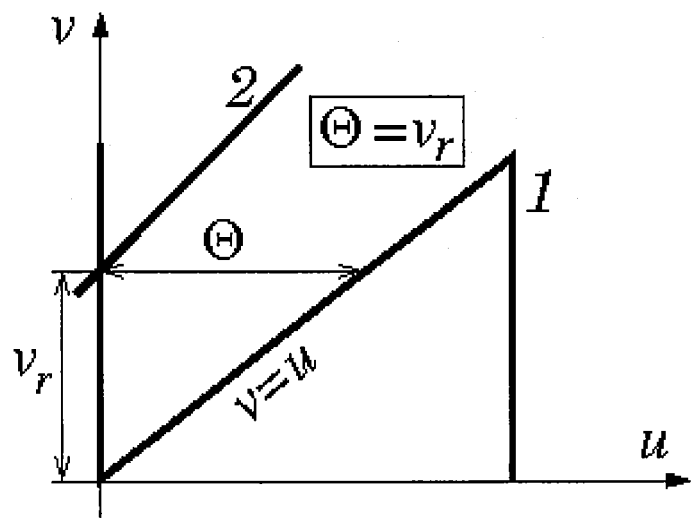
FIG. 2. Nullclines for the analytically solvable CSC reaction-diffusion model. Labels 1 and 2 mark nullclines for fast excitation (u) and slow recovery (v) processes, respectively. The N-shaped nullcline '1' incorporates v=u line, which implies the equality between the dimensionless excitation threshold $\Theta$ and the rest value $v_r$ of the recovery variable.

Parameter $v_r$ has double meaning in the CSC model. As seen above, $v_r$ is the rest value of the recovery variable v. However, it also serves as a measure of the threshold for excitation. This is because the middle branch of the u nullcline, which determines threshold, is a diagonal line v=u (FIG. 2). Therefore, in the dimensionless CSC model, the rest value of v and the excitation threshold are the same, and can be represented by a single parameter, $v_r$. In order for the model to support propagation of excitation waves, parameter $v_r$ must be below a certain value, $v_r^{crit}$. This "critical excitation threshold" can be computed analytically in the CSC model [Chernyak 1998a, 1998b].

Parameter $v_r$ and Cardiac Memory.

The CSC model as described by (1-2) does not represent the full dynamics of cardiac rhythm. In particular, it does not exhibit the gradual decrease of the AP duration that follows a stepwise increase in pacing rate and that proceeds with the time constant of approximately 30 s [Pitruzzello 2007]. Experiments in guinea pig and human ventricular muscle [Atwell 1981, Davidenko 1990, Ravens 1998] have shown that this manifestation of the "short-term cardiac memory" is accompanied by an exponential-like evolution of the excitation threshold. That observation motivates the modification of the CSC model aimed at introducing cardiac memory. Specifically, the excitation threshold $v_r$ becomes a dynamic variable governed by a first-order ODE, $$\frac{dv_r}{dt} = \frac{-v_r + v_r^\infty(T)}{\tau} \quad (3)$$

with $$v_r^\infty(T) = -\beta T + \alpha,$$

where $\tau$, $\alpha$, and $\beta$ are constants and $v_r^\infty$ (T) is the steady-state value of $v_r$ at the pacing period T. The first equation in (3) shows that, similar to experimental findings [Atwell 1981, Davidenko 1990], a stepwise change in pacing period from $T_1$ to $T_2$ results in a smooth exponential transition of the excitation threshold $v_r$ from $v_r^\infty(T_1)$ to $v_r^\infty(T_2)$. For the sake of simplicity, in (3) $v_r^\infty$ was chosen to be linearly dependent on the pacing period T.

Example 2

Data Collection, Processing and Construction of Restitution Portraits

The digitized original QT and RR interval signals can be recorded either during Cornell-type gradual exercise protocols or during electrophysiological (EP) studies with gradual electrical pacing. After resampling, these sequences can be used to determine the RPs. Custom software removes electrical noise and filters fluctuations and trends from the digitized signals using low-pass and high-pass frequency thresholds. The same software package can eliminate pacing stimuli without distortion of the filtered signals by implementing Daubechies 4$^{th}$ order wavelet [Starobin 2007].

For data acquired from the exercise test, we implement an adaptive least-mean square (LMS) algorithm to estimate QT interval fluctuations that are physiologically related to DI [Varadarajan 2009]. Using the output of the LMS filter, we compute a cross-correlation, CC, of this signal with DI fluctuations:

$$CC(n) = \frac{1}{\|QT_{lms}\|\|DI\|} \sum_{j=n-p}^{n+p} QT_{lms}(j)DI(j) \quad (4)$$

The S1-S2 and basic cycle length (BCL) restitution curves are determined from positively (CC>CC*) and negatively (CC<CC*) correlated portions of the interval signals, respectively (CC* is a correlation threshold).

Figure 4:
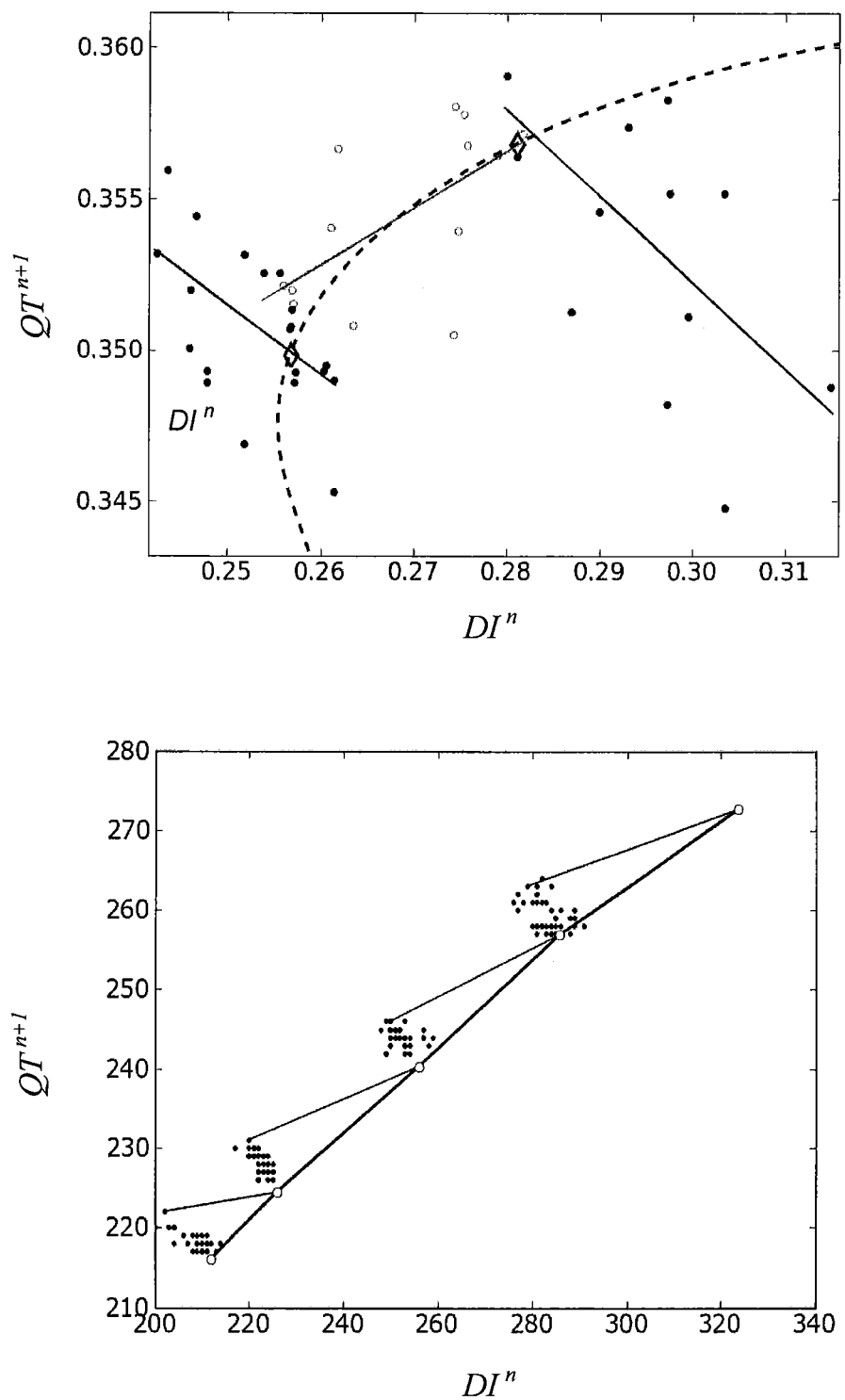
FIG. 4. An example of the restitution portraits (RPs), measured non-invasively during gradual exercise (left panel) and invasively in a pig during electrical pacing [Polotsky 2008]. Both RP plots show duration of $(n+1)^{th}$ QT interval ($QT^{n+1}$) as a function of the preceding diastolic interval (DI"). Black and light gray regression lines in the left panel show basic cycle length (BCL) and S1-S2 restitution curves for negatively and positively correlated portions of QT-DI fluctuations, respectively. Two steady-state points are determined by intersections between BCL curves and QT-DI trend shown in gray. Right panel shows the steady-state restitution curve (open circles connected by the bold line), portions of four positive S1-S2 restitution curves (thin lines), and four BCL curves with negative slopes (black circles).

RP is constructed as a sequence of regression lines with positive and negative slopes for S1-S2 and BCL restitution dependencies, respectively (FIG. 4, left panel). For EP studies, the RP is constructed by plotting the (n+1)$^{th}$ QT interval as a function of the n$^{th}$ DI interval as shown in FIG. 4 (right panel).

Example 3

Customizing Parameters of the CSC Model to RPs of Individual Patients

Figure 3:
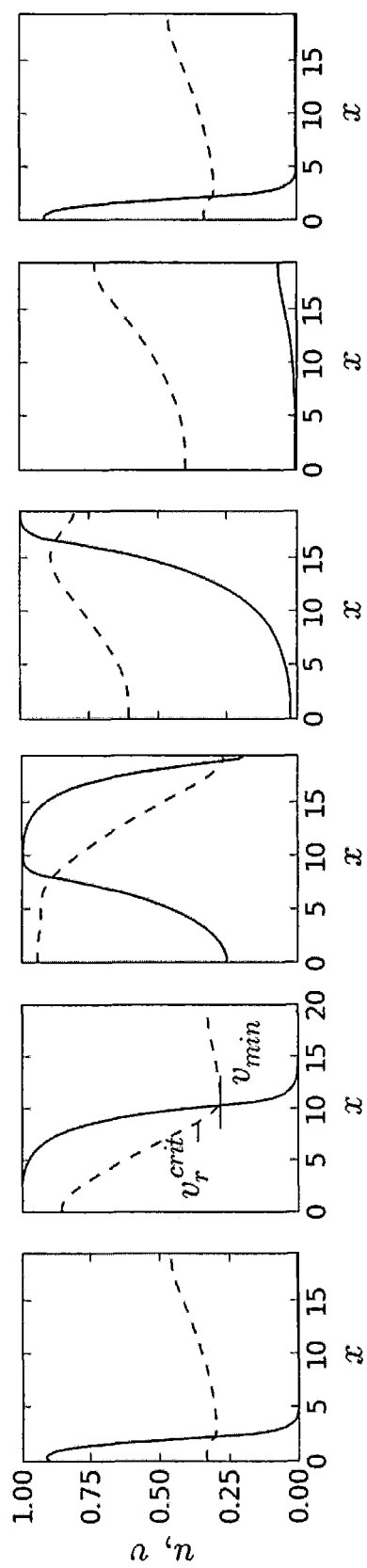
FIG. 3. Numerical solution of the CSC model that depicts formation and propagation of an AP between two successive pacing stimuli applied at the left end of the cable (x=0). Solid and dashed lines show spatio-temporal dynamics of u and v, respectively. The first and last snapshots correspond to the moments when the two successive pacing stimuli are applied. Time intervals between the snapshots are equal to 20% of the pacing period. Short horizontal lines in the second panel show values of $v_r^{crit}$ and $v_{min}$ ($v_r^\infty$=0.19, $v_{min}$=0.29, $\varepsilon$=0.1, T=9; measured in the middle of the cable).

To produce results comparable to experiments, the one-dimensional (i.e., 1D) cable with the CSC model was stimulated at the left end with pacing period T, and APD and DI values were measured in the middle of the cable (FIG. 3). For all optimization runs, dimensionless APD, DI, and T values obtained from the model were converted to units directly comparable to the experimental QT, TQ, and RR intervals using the following scaling:

$$\overline{QT} = \frac{C_m}{\sigma_{Na}} APD, \quad (5)$$

$$\overline{TQ} = \frac{C_m}{\sigma_{Na}} DI,$$

$$\overline{RR} = \frac{C_m}{\sigma_{Na}} T,$$

where $C_m$ and $\sigma_{Na}$ are characteristic values of membrane capacitance and sodium membrane conductance. A bar over a symbol indicates the data predicted by the model.

In order to determine the SoPR values for each patient, we choose parameters of the CSC model so that the RP from the model matches the RP measured in the EP study. The CSC model (1-3) has six parameters: $\epsilon$, $\zeta$, $\lambda$, $\tau$, $\alpha$, and $\beta$. Determining all six parameters simultaneously with a massive least-squares fit to the entire RP would have a hard time dealing with multiple minima or with large regions in parameter space that give a fit of essentially the same quality. Therefore, we determine parameters sequentially, in small groups, using our insight into the role of the individual parameters and building on our experience from previous studies [Schaeffer 2007]. We start with two simplifications. First, parameter $\lambda$, which determines the wavelength of the propagating AP, is set to a constant value of 0.23, which assures that the wavelength remains physiologically relevant in a wide range of pacing rates. Second, we eliminate from fitting parameters $\alpha$ and $\beta$ that determine the dependence of the excitation threshold $v_r^\infty$ on the pacing period T. Instead, we determine $v_r^\infty$ for each T separately. This approach avoids possible errors introduced by assuming in (3) the linear rate dependence of $v_r^\infty$ on T. Thus, two parameters $\alpha$ and $\beta$ are replaced by one rate-dependent parameter $v_r^\infty$.

After these initial simplifications, the model has four parameters ($\epsilon$, $\zeta$, $v_r^\infty$, $\tau$) that need to be determined for each pacing rate. The fitting procedure uses steady-state data from two consecutive pacing periods, $T^n$ and $T^{n+1}$, and all transient data collected after $T^n$ has been decreased to $T^{n+1}$. Fitting is performed in two steps, after recognizing that three of the parameters ($\varepsilon$, $\zeta$, $v_r^\infty$) control the steady-state values of QT intervals and one parameter ($\tau$) controls the memory transient.

Figure 5:
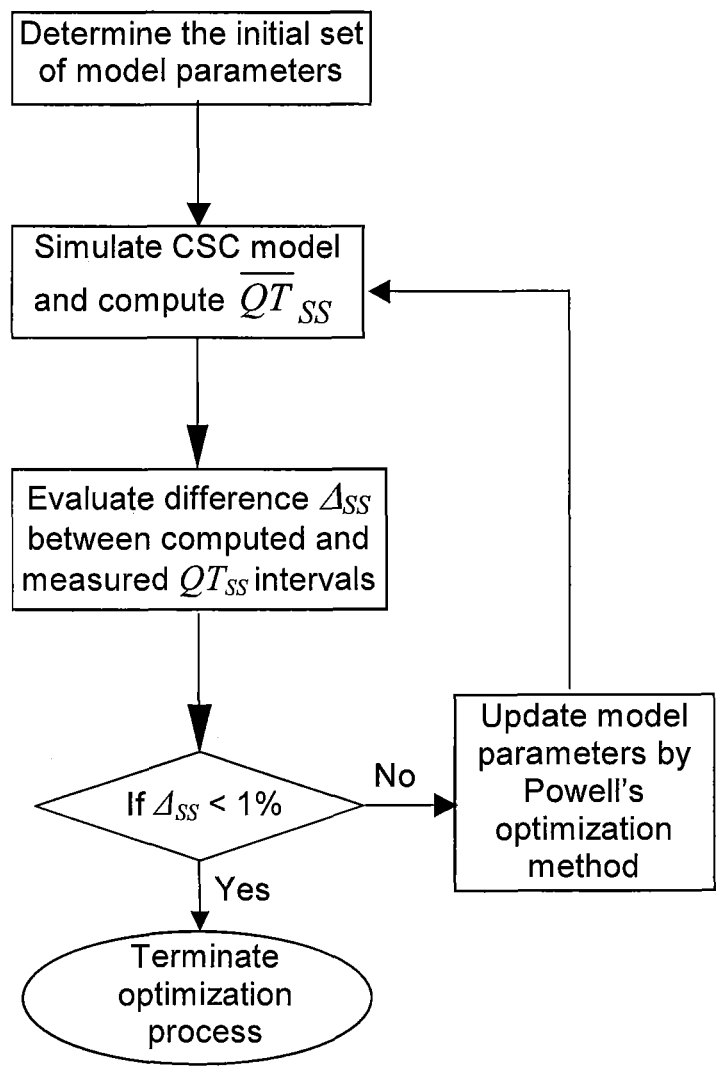
FIG. 5. Block-diagram of the first step of the iterative optimization method

The first step is illustrated in FIG. 5. The objective is to find values of ($\varepsilon$, $\zeta$, $v_r^\infty$) that minimize the difference between steady-state QT intervals computed by the model, $\overline{QT_{SS}}$, and the corresponding intervals from the experiment, $QT_{SS}$:

$$\Delta_{SS}(\varepsilon,\zeta,v_r) = |\overline{QT_{SS}} - QT_{SS}|^n + |\overline{QT_{SS}} - QT_{SS}|^{n+1}, \quad (6)$$

where superscripts $^n$ and $^{n+1}$ indicate data from pacing periods $T^n$ and $T^{n+1}$.

The initial approximation for parameters ($\varepsilon$, $\zeta$, $v_r^\infty$) is obtained by searching over a sparse 3D grid. The parameter set that yields the minimum value of $\Delta_{SS}$ are used as a starting point in the optimization illustrated in FIG. 5. Estimates of ($\varepsilon$, $\zeta$, $v_r^\infty$) are refined using Powell's iterative optimization technique [Press 1992]. At each iteration, the CSC model yields new values of $\overline{QT_{SS}}$, a value of $\Delta_{SS}$ is updated, and new estimates for ($\varepsilon$, $\zeta$, $v_r^\infty$) is obtained. Iterations are terminated when $\Delta_{SS}$ falls below 1%.

The second step determines the time constant $\tau$ of the short-term memory transient. Here, the objective is to minimize the difference $\Delta_{MT}$ between the computed and the measured estimates of the QT intervals during the multi-beat memory transient that follows the decrease of the pacing period from $T^{n+1}$ to $T^n$:

$$\Delta_{MT} = \sum_{i=1}^{N} |\overline{QT}_i - QT_i|, \quad (7)$$

where N is the number of beats in the exponential memory transient. The optimization procedure is the same as in step 1 (FIG. 5), adjusted to use Eq. (7) and the data from the memory transients. The two-step fitting procedure, repeated for every pacing rate T, yields estimates of model parameters for each T. That allows us to use the CSC model to compute the reserve of refractoriness as $$RoR = (v_r^{crit} - v_{min})/v_r^{crit} \times 100\% = (1 - v_{min}/v_r^{crit}) \quad (8)$$

and the rate of memory adaptation as $$RoM = T/\tau \quad (9)$$

The final metric, SoPR is formed by combining RoR and RoM. In the initial tests (Example 4), SoPR=RoR*RoM but other ways of forming SoPR are also possible.

Example 4

Changes in SoPR in Response to Reduced Myocardial Perfusion in Pigs

Preliminary results in support of the present invention come from the previous experimental study of the porcine model of coronary artery disease. The data shown below demonstrate that increased proarrhythmic states caused by reduced myocardial perfusion correlate with lower values of the SoPR.

Reduced myocardial perfusion was produced using graded flow reductions in the left anterior descending coronary artery of porcine hearts [Starobin 2007, Polotsky 2008]. Each heart was subjected to 3-7 randomized graded flow reductions, 20 min. in duration and separated by a minimum 45 min. reperfusion period. During each flow rate (FR), the pacing rate was incrementally accelerated in steps of 10 beats/min until a rate of 150 was achieved. Intracardiac ECG recordings were processed after the study to yield sequences of QT, DI, and RR interval durations. For each pacing rate, steady-state values of QT interval ($QT_{SS}$) and RR interval ($RR_{SS}$) were computed by averaging data collected during the last 40 seconds of pacing at that rate. Finally, data from all pacing rates for a given FR were combined into the RP as shown in the right panel in FIG. 4.

To produce results comparable to these experiments, the 1D cable with the CSC model was stimulated at the left end with pacing period T, and APD (QT) and DI values were measured in the middle of the cable (FIG. 3). For all optimization runs, dimensionless QT, DI, and T values obtained from the model were converted to units directly comparable to the experimental QT, DI, and RR intervals using scaling in Eq. (5). The values of parameters ($\varepsilon$, $\zeta$, $v_r^\infty$) of the CSC model were optimized using the procedure described in detail in Example 3. Two parameters were independent of the FR and varied very little between animals: $\varepsilon$ stabilized at 0.01 and $\zeta$ stabilized at a value close to unity. In contrast, parameter $v_r^\infty$ varied significantly, especially at reduced flow rates. Taking into consideration that FR is a relative measure, we used a normalized value of the SoPR defined as $SoPR_{norm} = SoPR/SoPR_0$, where $SoPR_0$ is the maximum value of SoPR determined for 100% flow rate in each experimental animal.

Figure 6:
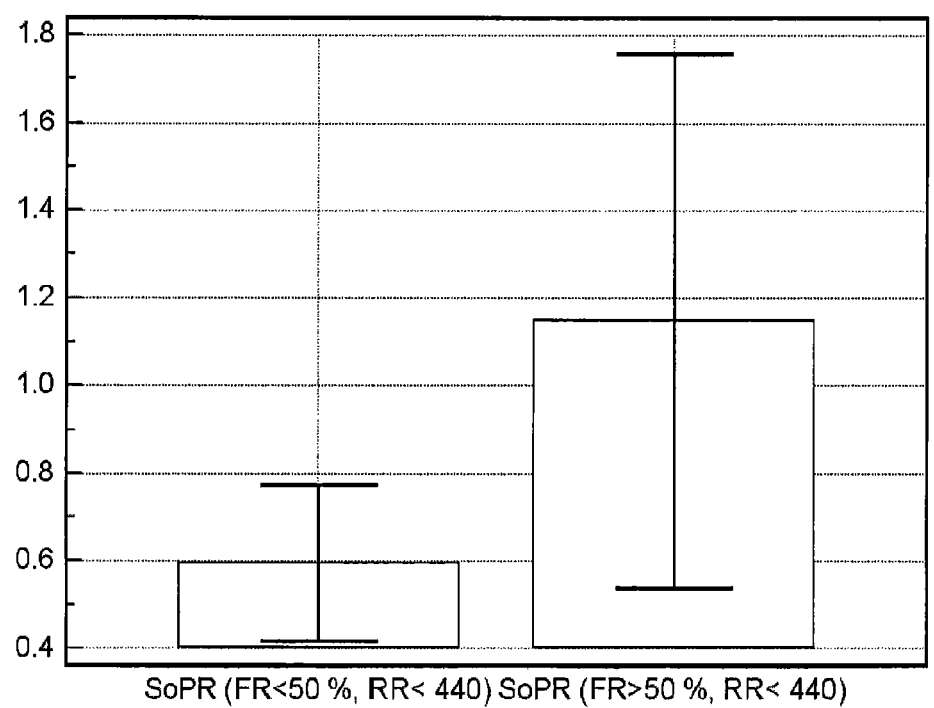
FIG. 6. Anova box-plot with 95% confidence interval (CI) values for normalized SoPR in groups with FR>50% and FR<50%.

FIG. 6 shows the estimates of $SoPR_{norm}$ from intramyocardial ECG recordings at elevated pacing rates, RR<430 ms. Separation of $SoPR_{norm}$ between the groups with FR greater and smaller than 50% is statistically significant (t-test with unequal variances, P=0.032).

FIG. 6 demonstrates that ischemia lowers $SoPR_{norm}$, which indicates the increased proximity to the onset of propagation instabilities. This result was expected, as ischemia is one of the conditions that increase risk for arrhythmias. Since this population of patients at risk is often missed by other metrics, such as TWA [Kusmirek & Gold 2007], the method of present invention may be able to fill this gap.

Example 5

Changes in RoR and Minimal Level of Refractoriness in Response to Reduced Diastolic Intervals Additional observations in support of the present invention come from our ongoing American Heart Association sponsored clinical study "Correlation between onset of rhythm instabilities and the stability-of-propagation reserve metric in patients" (10CRP3040018), which is currently taking place at Duke Medical Center Cardiac Electrophysiology Laboratory. The data shown below have been acquired during invasive electrophysiological procedures in patients referred for cardiac atrial ablation.

Figure 7:
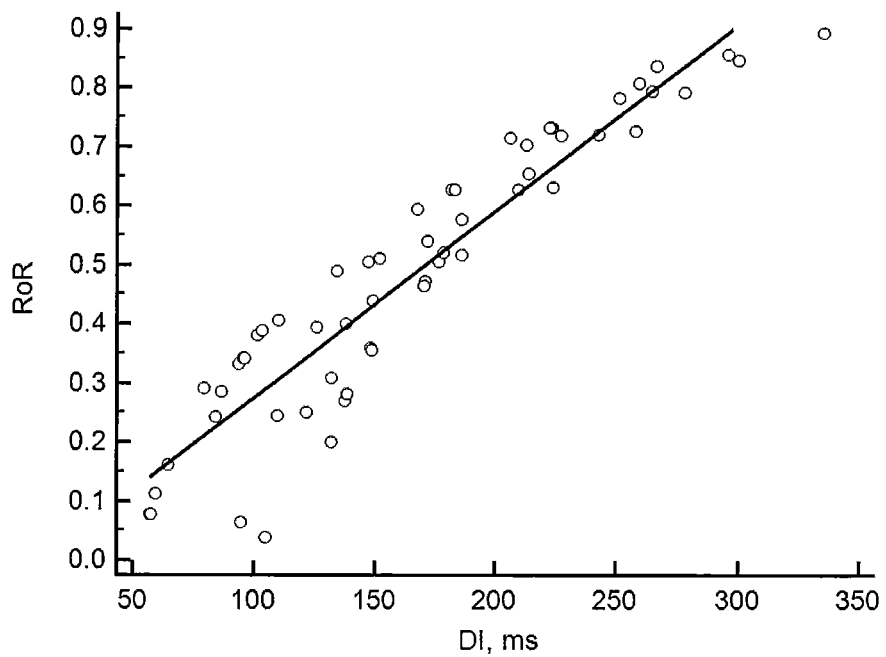
FIG. 7 Examples of complementary dependences of RoR (Panel A) and minimal level of refractoriness Vmin (Panel B) on diastolic intervals for six patients referred for atrial ablation in the Duke Medical Center Cardiac Electrophysiology Lab.
Figure 7:
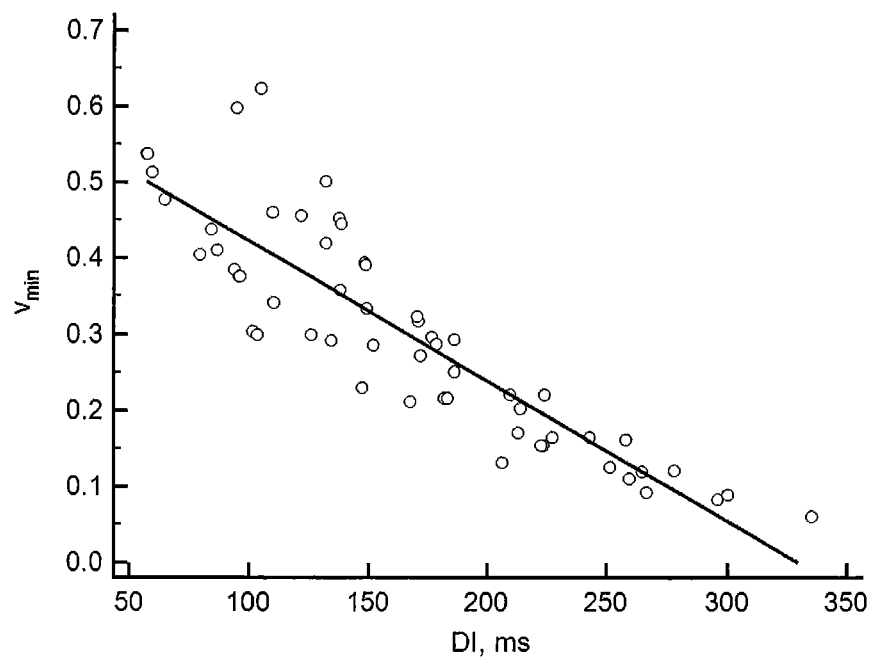

As a part of the procedure patient's heart was decrementally paced in a step-wise manner starting from RR=650 ms. The shortest pacing plateau was equal to 350 ms. Correspondingly, diastolic intervals decreased from 350 ms to 100 ms, which according to [Kusmirek & Gold 2007] should elevate susceptibility to unstable cardiac rhythm. Indeed, FIG. 7 shows expected decrease of reserve of refractoriness, RoR, (Panel A, Eq. 8) and increase of a minimal level of refractoriness, $v_{min}$ (Panel B) for shorter diastolic intervals.

REFERENCES

D. Attwell, I. Cohen, D. Eisner, The effects of heart rate on the action potential of guinea-pig and human ventricular muscle, J. Physiol., 313: 439-461, 1981.

Y. B. Chernyak, J. M. Starobin, R. J. Cohen, Class of exactly solvable models of excitable media, Phys. Rev. Lett., 80: 5675-5678, 1998a.

Y. B. Chernyak, J. M. Starobin, R. J. Cohen, Where do dispersion curves end? A basic question in theory of excitable media, Phys. Rev. E, 58: R4108-R4111, 1998b.

J. P. Daubert, W. Zareba, W. J. Hall, et al., Predictive value of ventricular arrhythmia inducibility for subsequent ventricular tachycardia or ventricular fibrillation in Multicenter Automatic Defibrillator Implantation Trial (MADIT) II patients, J. Am. Coll. Cardiol. 47: 98-107 2006.

J. Davidenko, R. Levi, G. Maid, M. Elizari, M. Rosenbaum, Rate dependence and supernormality in excitability of guinea pig papilary muscle, Am. J. Physiol.-Heart and Circul. Physiol., 259: H290-H299, 1990.

F. H. Fenton, E. M. Cherry, H M. Hastings, S. J. Evans, Multiple mechanisms of spiral wave breakup in a model of cardiac electrical activity, Chaos, 12: 852-892, 2002.

M. R. Franz, The electrical restitution curve revisited: steep or flat slope—Which is better?, J. Cardiovasc. Electrophysiol., 14: S140-S147, 2003.

M. Haghjoo, A. Arya, M. A. Sadr-Ameli, Microvolt T-wave alternans: A review of techniques, interpretation, utility, clinical studies, and future perspectives, Int. J. Cardiol., 109: 293-306, 2006.

R. E. Ideker, J. M. Rogers, R. M. Gray, Steepness of the restitution curve: A slippery slope? J. Cardiovasc. Electrophysiol., 13: 1173-1175, 2002.

S. S. Kalb, H. Dobrovolny, E. Tolkacheva, S. F. Idriss, W. Krassowska, D. J. Gauthier, The restitution portrait: A new method for investigating rate-dependent restitution, J. Cardiovasc. Electrophysiol., 15: 698-709, 2004.

S. L. Kusmirek, M. R. Gold, Sudden cardiac death: The role of risk stratification, Am. Heart J., 153: S25-S33, 2007.

D. Lloyd-Jones, R. Adams, M. Carnethon, et al., Heart disease and stroke statistics 2009 update. A report from the American Heart Association Statistics Committee and Stroke Statistics Subcommittee, Circulation, 119: pp. e1-e161, 2009.

R. C. Myles, F. L. Burton, S. M. Cobbe, G. L. Smith, The link between repolarisation alternans and ventricular arrhythmia: Does the cellular phenomenon extend to the clinical problem?, J. Mol. Cell. Cardiol., 45: 1-10, 2008.

A. M. Pitruzzello, S. F. Idriss, W. Krassowska, Spatial heterogeneity of the restitution portrait in rabbit epicardium, Am. J. Physiol., 292: H1568-H1578, 2007.

V. N. Polotski, V. Varadarajan, A. J. Starobin, C. P. Danford, W. E. Cascio, T. A. Johnson, J. M. Starobin, Relation between cardiac restitution and flow limitation in an experimental model of coronary artery disease, J. Electrocardiol., 41: 646, 2008.

W. H. Press, S. A. Teukolsky, W. T. Vetterling, B. P. Flannery, Numerical Recipies in Fortran 77, Cambridge Press, 1992.

U. Ravens, E. Wettwer, Electrophysiological aspects of changes in heart rate, Basic Res. Cardiol., 93, Suppl. 1: 60-65, 1998.

D. G. Schaeffer, J. W. Cain, D. J. Gauthier, S. S. Kalb, W. Krassowska, R. A. Oliver, E. G. Tolkacheva, An ionically based mapping model with memory for cardiac restitution, Bull. Math. Biol., 69: 459-482, 2007.

J. M Starobin, Y. I. Zilberter, E. M. Rusnak, C. F. Starmer, Wavelet formation in excitable cardiac tissue: The role of wavefront-obstacle interaction in initiating high-frequency fibrillatory-like arrhythmias, Biophys. J., 70: 581-594, 1996.

J. M. Starobin, W. E. Cascio, A. H. Goldfarb, V. J, Varadarajan, A. J. Starobin, C. P. Danford, T. A. Johnson, Identifying coronary artery flow reduction and ischemia using quasistationary QT/RR-interval hysteresis measurements, J. Electrocard., 40: S91-S96, 2007.

J. M. Starobin, C. P. Danford, V. Varadarajan, A. J. Starobin, V. N. Polotski, Critical scale of propagation influences dynamics of waves in a model of excitable medium, Nonlinear Biomedical Physics, vol. 3, art. 4, 2009.

V. Varadarajan, V. N. Polotski, C. P. Danford, A. J. Starobin, J. M. Starobin, Assessing QT-RR interval hysteresis in 12-lead electrograms, In Proceedings: Computing in Cardiology, 36:273-276, 2009.

That which is claimed is:

1. A method of determining the susceptibility to ventricular arrhythmias in a subject, comprising the steps of:
    (a) collecting at least one QT and DI interval data set from the subject during a stage of gradually increasing heart rate or a stage of gradually decreasing heart rate;
    (b) estimating QT interval fluctuations, DI interval fluctuations and QT-DI trends by applying an adaptive least-mean square filter to the QT and DI interval data set;
    (c) calculating a cross-correlation of the QT interval fluctuations with DI fluctuations to determine correlated and anti-correlated portions of the QT and DI interval data set;
    (d) determining corresponding regression lines for said correlated and anti-correlated portions;
    (e) finding a plurality of steady state QT-DI points designated by intersections between said QT-DI trends and said corresponding regression lines;
    (f) fitting action potential durations computed from a rate dependent reaction-diffusion model to corresponding ones of said steady state QT-DI points to give (i) a model excitation threshold and (ii) a minimal level of refractoriness at a plurality of said steady state QT-DI points;
    (g) at a steady state QT-DI point corresponding to a highest heart rate in said QT and DI interval data set, determining a difference between said minimal level of refractoriness and a model critical excitation threshold for a stable solitary pulse corresponding to the rate dependent reaction diffusion model of step (f) to give a reserve of refractoriness (RoR);
    (h) fitting action potential durations computed from the rate dependent reaction-diffusion model to said correlated and anti-correlated portions to give a rate of adaptation of each model excitation threshold to a corresponding steady state value at a plurality of said steady state QT-DI points;
    (i) at the steady state QT-DI point corresponding to the highest heart rate in said QT and DI interval data set, determining an inverse of said rate of adaptation to give a reserve of memory (RoM);
    (j) combining said reserve of refractoriness (RoR) and said reserve of memory (RoM) to produce a metric of stability-of-propagation reserve (SoPR) in said subject, a higher value of SoPR indicating lower susceptibility to ventricular arrhythmias in said subject;
    (k) generating a risk of ventricular arrhythmia in the subject based on the metric of stability-of-propagation reserve (SoPR); and
    (l) administering therapy on the subject based on the generated risk of ventricular arrhythmia in the subject.

2. The method of claim 1, wherein said step (a) of collecting at least one QT and DI interval data set is carried out by surface EKG or intracardiac EKG.

3. The method of claim 1, wherein said step (b) of estimating is carried out by applying low- and high pass filtering.

4. The method of claim 1, wherein said step (d) of determining corresponding regression lines for said correlated and anti-correlated portions is carried out by linear regression analysis.

5. The method of claim 1, wherein said action potential durations are from 100 to 900 milliseconds in duration.

6. The method of claim 1, wherein said model excitation threshold (dimensionless) is from 0.05 to 1.

7. The method of claim 1, wherein said minimal level of refractoriness (dimensionless) is from 0.05 to 1.

8. The method of claim 1, wherein said highest heart rate in said QT and DI interval data set is 300 beats per minute.

9. The method of claim 1, wherein said model critical excitation threshold for a stable solitary pulse (dimensionless) is from 0.1 to 1.

10. The method of claim 1, wherein said reserve of refractoriness (dimensionless) is from zero to one.

11. The method of claim 1, wherein said rate of adaptation of each model excitation threshold (dimensionless) is 0.01 to 1.

12. The method of claim 1, wherein said reserve of memory (dimensionless) is from 1 to 100.

13. The method of claim 1, wherein said stability-of-propagation reserve (dimensionless) is from zero to one.

14. A method of determining susceptibility to ventricular arrhythmias in a subject, comprising the steps, performed on a computer system, of:
   (a) providing at least one QT and DI interval data set collected from the subject during a stage of gradually increasing heart rate or a stage of gradually decreasing heart rate;
   (b) estimating QT interval fluctuations, DI interval fluctuations and QT-DI trends by applying an adaptive least-mean square filter to the QT and DI interval data set;
   (c) calculating a cross-correlation of the QT interval fluctuations with DI fluctuations to determine correlated and anti-correlated portions of the QT and DI interval data set;
   (d) determining corresponding regression lines for said correlated and anti-correlated portions;
   (e) finding a plurality of steady state QT-DI points designated by intersections between said QT-DI trends and said corresponding regression lines;
   (f) fitting action potential durations computed from a rate dependent reaction-diffusion model to corresponding ones of said steady state QT-DI points to give (i) a model excitation threshold and (ii) a minimal level of refractoriness at a plurality of said steady state QT-DI points;
   (g) at a steady state QT-DI point corresponding to a highest heart rate in said QT and DI interval data set, determining a difference between said minimal level of refractoriness and a model critical excitation threshold for a stable solitary pulse corresponding to the rate dependent reaction diffusion model of step (f) to give a reserve of refractoriness (RoR);
   (h) fitting action potential durations computed from the rate dependent reaction-diffusion model to said correlated and anti-correlated portions to give a rate of adaptation of each model excitation threshold to a corresponding steady state value at a plurality of said steady state QT-DI points;
   (i) at the steady state QT-DI point corresponding to the highest heart rate in said QT and DI interval data set, determining an inverse of said rate of adaptation to give a reserve of memory (RoM);
   (j) combining said reserve of refractoriness (RoR) and said reserve of memory (RoM) to produce a metric of stability-of-propagation reserve (SoPR) in said subject, a higher value of SoPR indicating lower susceptibility to ventricular arrhythmias in said subject;
   (k) generating a risk of ventricular arrhythmia in the subject based on the metric of stability-of-propagation reserve (SoPR); and
   (l) administering therapy on the subject based on the generated risk of ventricular arrhythmia in the subject.

15. The method of claim 14, wherein said step (b) of estimating is carried out by applying low- and high pass filtering.

16. The method of claim 14, wherein said step (d) of determining corresponding regression lines for said correlated and anti-correlated portions is carried out by linear regression analysis.

17. The method of claim 14, wherein:
   said action potential durations are from 100 to 900 milliseconds in duration;
   said model excitation threshold (dimensionless) is from 0.05 to or 1;
   said minimal level of refractoriness (dimensionless) is from 0.05 to 1;
   said highest heart rate in said QT and DI interval data set is 300 beats per minute;
   said model critical excitation threshold for a stable solitary pulse (dimensionless) is from 0.1 to 1;
   said reserve of refractoriness (dimensionless) is from zero to one;
   said rate of adaptation of each model excitation threshold (dimensionless) is 0.01 to 1;
   said reserve of memory (dimensionless) is from 1 to 100; and
   said stability-of-propagation reserve (dimensionless) is from zero to one.

* * * * *

UNITED STATES PATENT AND TRADEMARK OFFICE
CERTIFICATE OF CORRECTION

PATENT NO. : 10,076,259 B2
APPLICATION NO. : 15/134881
DATED : September 18, 2018
INVENTOR(S) : Starobin et al.

Page 1 of 1

It is certified that error appears in the above-identified patent and that said Letters Patent is hereby corrected as shown below:

In the Specification

Column 6, Line 29: Please correct "(DI″)" to read -- (DI″) --

Column 8, Line 18: Please correct "$\Sigma_{ext}$" to read -- $\tau_{ext}$ --

Signed and Sealed this
Twelfth Day of March, 2019

Andrei Iancu
*Director of the United States Patent and Trademark Office*